United States Patent [19]

Tai

[11] Patent Number: 5,374,684
[45] Date of Patent: Dec. 20, 1994

[54] METHOD FOR MAKING AGGREGATES OR CLUSTERS OF WATER-SWELLABLE POLYMERS HAVING INCREASED HYDRATION RATE OVER UNASSOCIATED WATER-SWELLABLE POLYMERS

[75] Inventor: Eva F. Tai, Midland, Mich.

[73] Assignee: The Dow Chemical Company, Midland, Mich.

[21] Appl. No.: 115,332

[22] Filed: Sep. 1, 1993

Related U.S. Application Data

[60] Division of Ser. No. 929,071, Aug. 12, 1992, which is a continuation-in-part of Ser. No. 644,357, Jan. 18, 1991, abandoned, which is a continuation-in-part of Ser. No. 304,616, Jan. 24, 1989, abandoned.

[51] Int. Cl.$^5$ .................. C08F 6/24; C08F 265/02; C08F 265/04
[52] U.S. Cl. .................. 525/254; 525/242; 525/293; 525/296; 525/301; 525/303; 525/305; 524/458; 524/460; 524/529; 524/533; 524/534; 524/535
[58] Field of Search ............... 525/242, 254, 293, 296, 525/301, 303, 305; 524/458, 460, 529, 533, 534, 535

[56] References Cited

U.S. PATENT DOCUMENTS

| | | | |
|---|---|---|---|
| 5,002,986 | 3/1991 | Fujiuri et al. | 524/47 |
| 5,102,597 | 4/1992 | Roe et al. | 264/126 |
| 5,124,188 | 6/1992 | Roe et al. | 428/72 |
| 5,149,334 | 9/1992 | Lahrman et al. | 604/367 |
| 5,171,781 | 12/1992 | Farrar et al. | 524/547 |
| 5,180,622 | 1/1993 | Berg et al. | 428/192 |

FOREIGN PATENT DOCUMENTS

| | | |
|---|---|---|
| 0233014 | 8/1987 | European Pat. Off. |
| 9115368 | 10/1991 | WIPO |

*Primary Examiner*—Romulo H. Delmendo
*Attorney, Agent, or Firm*—John H. Roberts; Ronald G. Brookens

[57] ABSTRACT

Clusters of water-swellable polymer particles, having high rates of absorbency without gel-blocking are prepared by suspending water-swellable polymer particles in an inert hydrophobic liquid, such as hydrocarbon, and slowly adding to the particles a suspension of an aqueous solution optionally containing an $\alpha,\beta$-ethylenically unsaturated monomer in an inert hydrophobic liquid.

7 Claims, 10 Drawing Sheets

METHOD FOR MAKING AGGREGATES OR CLUSTERS OF WATER-SWELLABLE POLYMERS HAVING INCREASED HYDRATION RATE OVER UNASSOCIATED WATER-SWELLABLE POLYMERS

This is a divisional of application Ser. No. 07/929,071 filed Aug. 12, 1992, pending, which is a continuation-in-part of U.S. patent application Ser. No. 07/644,357 filed Jan. 18, 1991, abandoned, which was a continuation-in-part of U.S. patent application Ser. No. 07/304,616 filed Jan. 24, 1989, abandoned.

BACKGROUND OF THE INVENTION

Water-swellable polymers are well known in the art as useful in personal care products such as diapers and various other devices where aqueous absorption is desired. Water-swellable polymers are often produced as a powder or particulate. During the production of such polymer, a variety of particle sizes are produced. Despite the large surface area afforded by a plurality of fine particles, e.g., particles smaller than about 100 microns, such particles do not absorb moisture as desirably as larger polymer particles. Absorption of liquid by fine particles is adversely impacted by gel blocking, whereby an aqueous solution contacted with a polymer mass does not have access to all the polymer particles of the polymer mass, because of dense packing of the particles and gelling at the surfaces of the polymer mass. Accordingly, such fine particles are often separated from the product stream and discarded from the desirable larger particles.

Therefore, it would be desirable to create a product and method of manufacture whereby such fine particles could be recycled or reformed into useful water-absorbing polymer particles, rather than being discarded. It would further be desirable to create a product which capitalizes on the high surface area afforded by a plurality of fine particles, without exhibiting detrimental gel blocking.

SUMMARY OF THE INVENTION

The invention includes a composition comprising discrete clusters of water-swellable polymer particles associated to each other in a random packing configuration by a bonding component, said particles being spatially distributed to allow aqueous absorption, wherein at least about 70 percent of said particles are smaller than about 150 microns, and wherein said bonding component is the residue of an aqueous solution optionally containing an $\alpha,\beta$-ethylenically unsaturated monomer, such that the ratio of $\alpha,\beta$-ethylenically unsaturated monomer to particles within said composition is less than about 1:2.

The invention also includes a method for preparing water-swellable polymer clusters for absorbing aqueous fluids, comprising:

(a) suspending an aqueous solution and an amorphous oil dispersible substantially water-insoluble particulate suspending aid in an inert hydrophobic liquid to form a first suspension;

(b) suspending water-swellable polymer particles in an inert hydrophobic liquid to form a second suspension; and (c) slowly adding said first suspension, under agitation and polymerization conditions, to said second suspension, such that said particles are bonded to each other, whereby said discrete clusters of said particles are formed.

Optionally, the method may include the additional steps of (d) drying the clusters; (e) adding a wetting agent to the clusters; and (f) crushing the clusters.

The invention also includes absorbent articles, comprising:

(a) a hydrophilic fiber material; and
(b) clusters of water swellable polymers, formed by (i) preparing a first suspension of an aqueous solution and an amorphous, oil dispersible, substantially water-insoluble particulate suspending aid in an inert hydrophobic liquid to form a first suspension, and (ii) slowly adding said first suspension, under polymerization conditions, to a second suspension of water-swellable polymer particles in an inert hydrophobic liquid, and (iii) drying said clusters, wherein said particles are bonded together in a random packing configuration, said particles being spatially distributed to allow aqueous fluid absorption interior to said clusters by said particles without gel blocking at the exterior surfaces of said clusters, wherein said clusters have a vortex rate less than about 20 seconds (vortex rate being determined as described below).

BRIEF DESCRIPTION OF THE DRAWINGS

The Figures included herewith illustrate the invention by means of pairs of photomicrographs of the unassociated particles and the aggregates or clusters, of said particles. The actual invention is represented by the clusters shown in FIGS. 2, 4, 6, 8 and 10.

FIG. 1 is a photograph of unassociated water-swellable polymer particles having a size of 325 mesh (44 microns) and smaller and;

FIG. 3 is a photograph of unassociated particles having a variety of sizes and;

FIG. 5 is a photograph of unassociated polymer particles having a size of 170 to 325 mesh (88 to 44 microns) and;

FIG. 7 is a photograph of unassociated polymer particles having a size of 100 to 170 mesh (149 to 88 microns) and;

FIG. 9 is a photograph of unassociated polymer particles having a size of 50 to 100 mesh (297 to 149 microns) and;

DETAILED DESCRIPTION OF THE INVENTION

A. The Water-Swellable Polymer Particles

Figure 1:
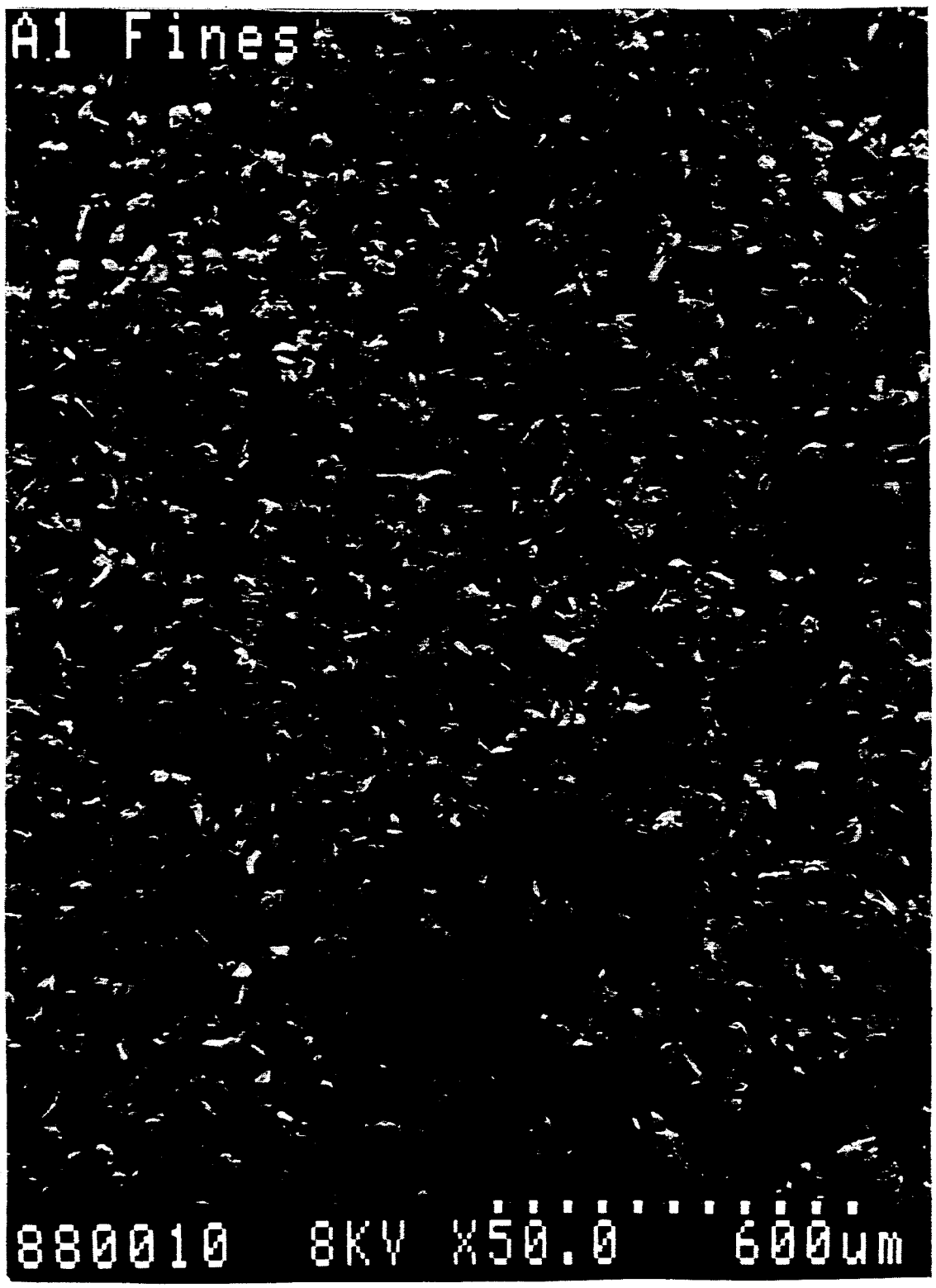
FIGS. 1, 3, 5, 7 and 9 depict the unassociated particles, and are not photographs of the present invention.
Figure 2:
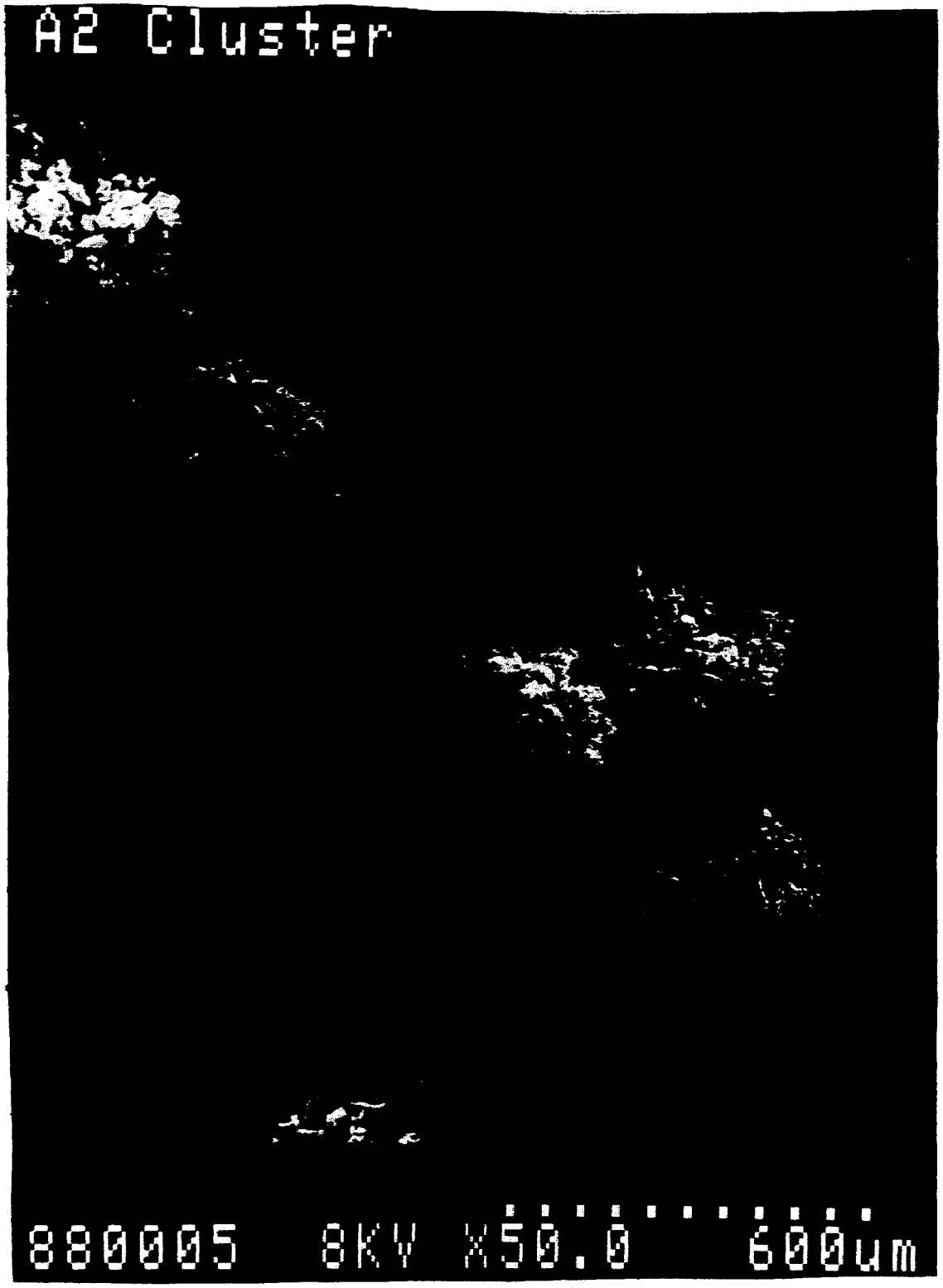
FIG. 2 is a photograph of the aggregates or clusters of the unassociated particles having the particle size of 325 mesh (44 microns) and smaller.
Figure 3:
Figure 4:
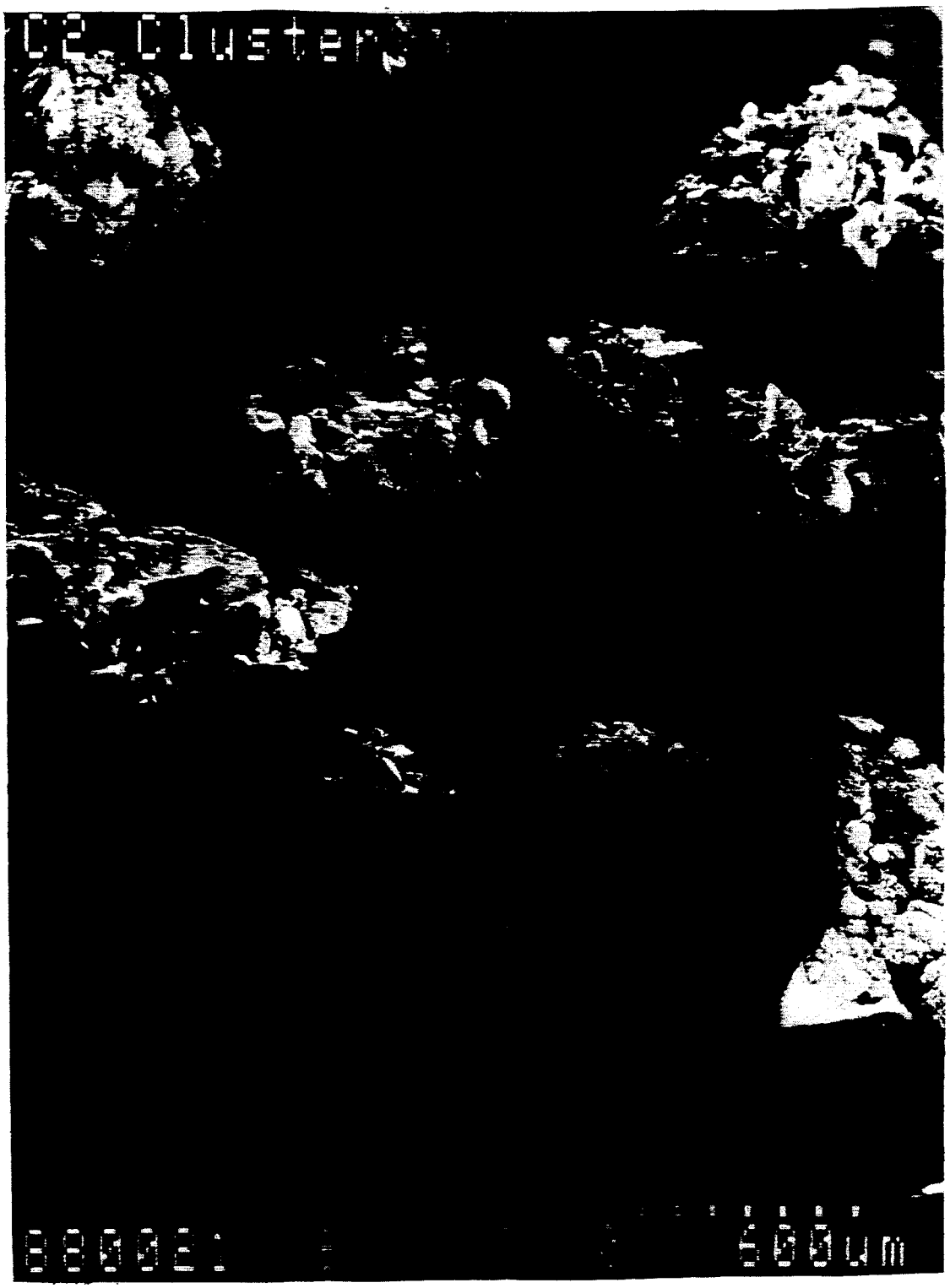
FIG. 4 is a photograph of the aggregates of those unassociated particles having varying sizes.
Figure 5:
Figure 6:
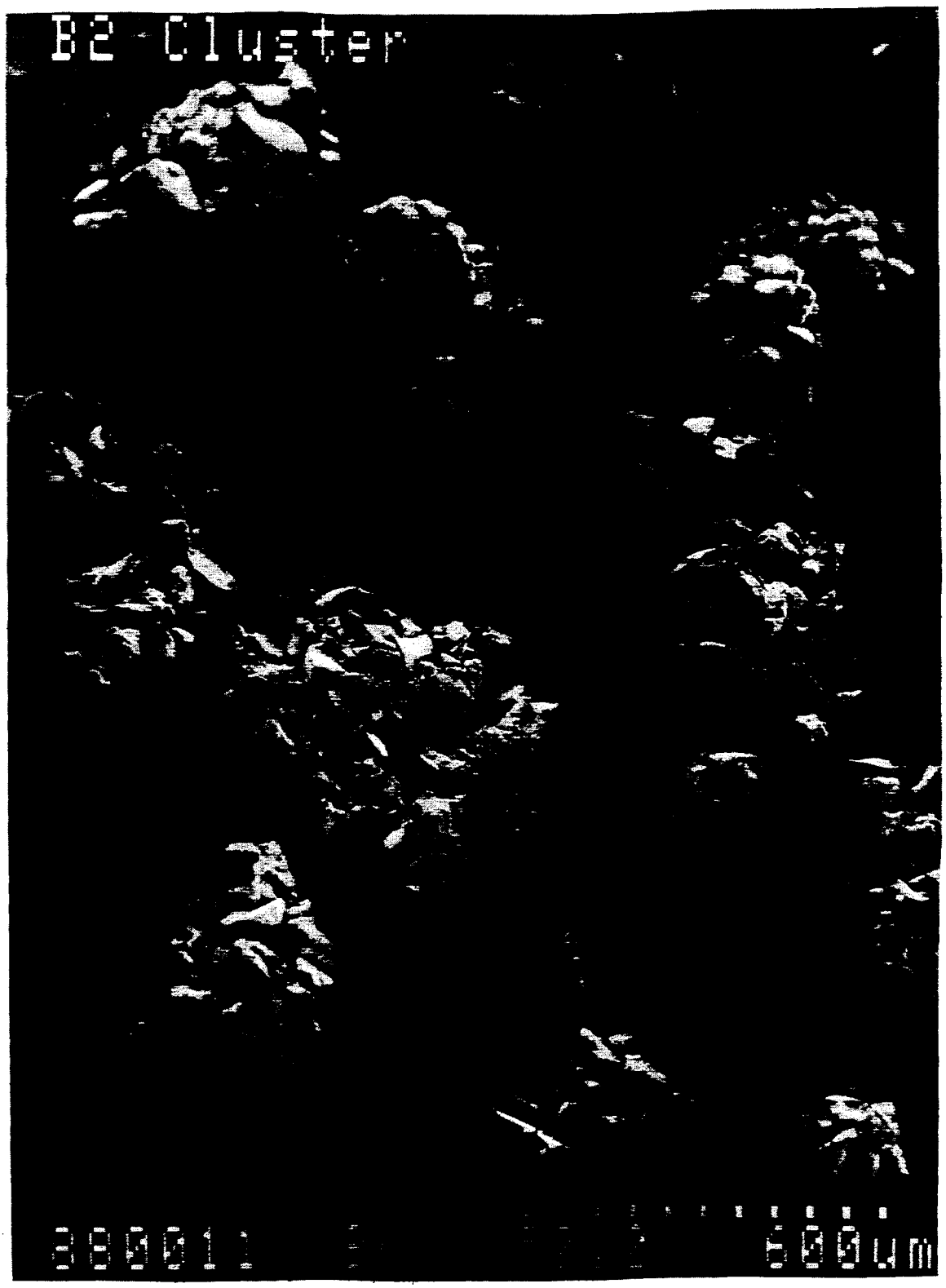
FIG. 6 is a photograph of the clusters of the polymer particles having an unassociated particle size of 170 to 325 mesh (88 to 44 microns).
Figure 7:
Figure 8:
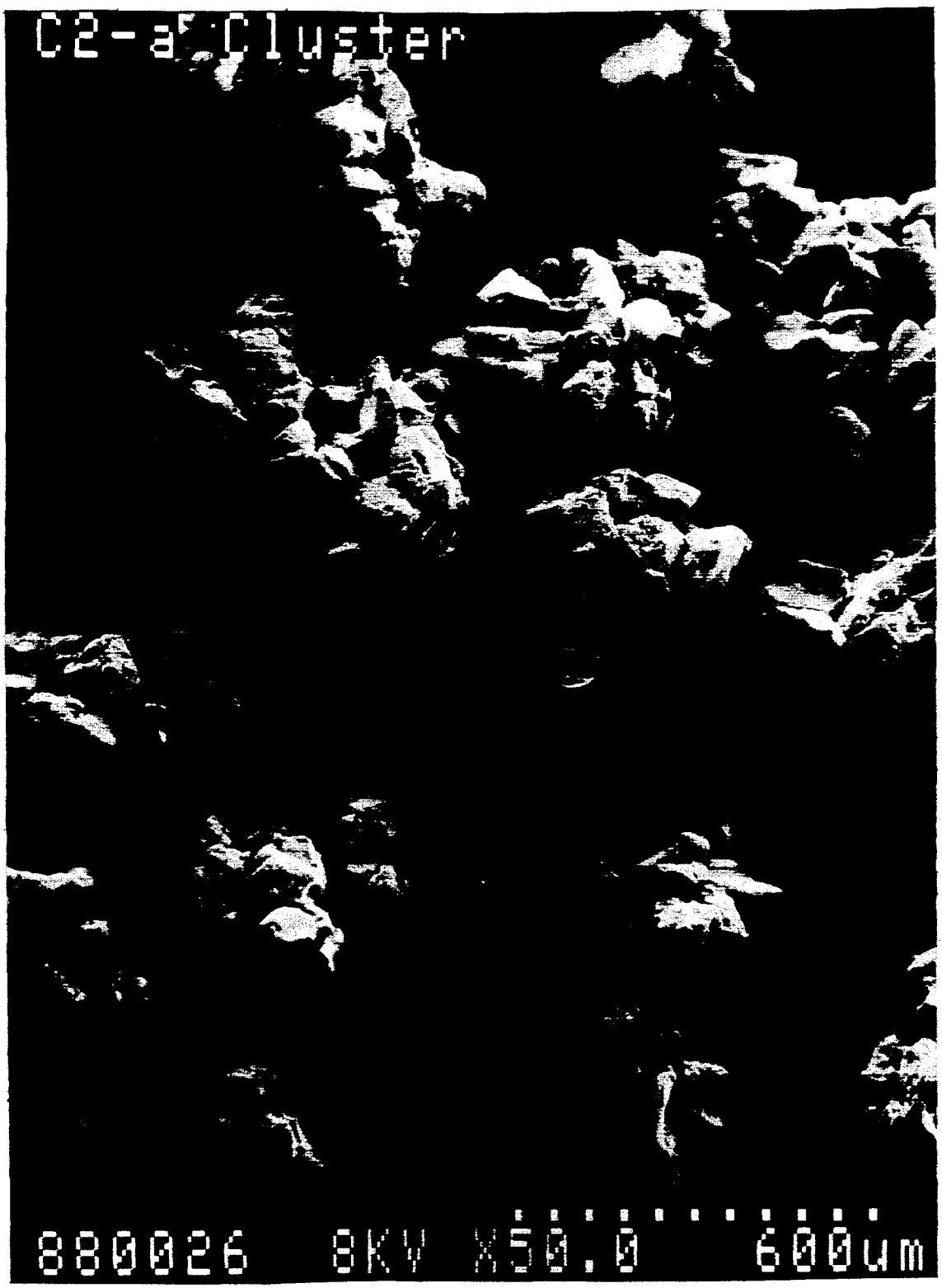
FIG. 8 is a photograph of the clusters of the polymer particles having an unassociated particle size of 100 to 170 mesh (149 to 88 microns).

The water-swellable or lightly crosslinked hydrophilic polymer particles useful in the present invention comprise any of the known hydrophilic polymers which are capable of absorbing large quantities of fluids. Examples of such polymers include those disclosed in U.S. Pat. Nos. 4,833,222, 3,997,484; 3,926,891; 3,935,099; 4,090,013; and 4,190,562. Such hydrophilic polymers are prepared from water-soluble $\alpha,\beta$-ethylenically unsaturated monomers such as mono and polycarboxylic acids and acrylamide and its derivatives.

The water-soluble monomers which are polymerized to form the water-swellable polymers of the present invention include those monomers listed in U.S. Pat. No. 4,833,222. Examples of such monomers include $\alpha,\beta$-ethylenically unsaturated monomers such as mono and polycarboxylic acids.

B. The Aggregates or Clusters

The term "clusters or aggregates" in this application means discrete clusters of water-swellable polymer particles, each cluster permeated with many channels or the like wherein a contacting aqueous fluid may penetrate into the interior of said cluster such that the fluid is absorbed by the individual polymer particles of said cluster.

Water-swellable or lightly crosslinked hydrophilic polymer particles which benefit from being incorporated into the aggregates of clusters of the present invention are those unassociated particles which have a particle size less than about 100 mesh (150 microns). The water-swellable or lightly crosslinked hydrophilic polymer particles which most benefit from being incorporated into the aggregates or clusters of the present invention are those unassociated particles which have a particle size less than about 150 mesh (100 microns), and which preferably have a particle size between about 150 mesh (100 microns) and about 400 mesh (37 microns). Such unassociated particles have been identified as causing gel blocking, as described above. In contrast, these same particles do not exhibit gel blocking behavior when incorporated into the aggregates or clusters of the present invention. As such, the aggregates or clusters of the invention utilize the high surface area afforded by the particles. Moreover, the increased size of the aggregates as opposed to the particles facilitates their retention in an absorbent structure, such as a diaper.

The clusters of water-swellable polymers of the invention comprise water-swellable polymer particles associated by being bound to other water-swellable polymer particles in a random packing configuration spatially distributed to allow aqueous absorption. The packing configuration of the polymer particles described herein as "random packing configuration spatially distributed to allow aqueous absorption" is illustrated in the photographs, FIGS. 2, 4, 6, 8 and 10. The Figures illustrate the particles of the aggregates or clusters as being bonded together in a random spatial distribution to allow for greater efficiency of aqueous absorption.

C. The Suspension of the Aqueous Solution (The First Suspension)

The first suspension comprises a suspension of an aqueous solution in an inert hydrophobic liquid, the aqueous solution being useful to promote association between adjacent polymer particles. The first suspension will preferably include a particulate suspending aid, useful to stabilize the suspension of the aqueous solution in the inert hydrophobic liquid. However, the particulate suspending aid may be omitted from the first suspension; most preferably, in this case the particulate suspending aid will be provided in the second suspension.

The inert hydrophobic liquid used to suspend the aqueous solution of monomer is usually an organic compound which is normally liquid at the conditions at which the polymerization process occurs. Operable liquids include hydrocarbons or substituted hydrocarbons. Preferred organic liquids are the halogenated hydrocarbons such as perchloroethylene, methylene chloride and the like, as well as liquid hydrocarbons having from 4 to 15 carbons per molecule, including aromatic and aliphatic hydrocarbons and mixtures thereof, e.g., benzene, xylene, toluene, mineral oils, liquid paraffins such as kerosene, naphtha and the like. Of the foregoing organic liquids, the hydrocarbons are the more preferred, with aliphatic hydrocarbons being most preferred.

The aqueous solution useful to promote association between adjacent polymer particles optionally comprises an $\alpha,\beta$-ethylenically unsaturated monomer. When the aqueous solution comprises an $\alpha,\beta$-ethylenically unsaturated carboxylic acid monomer, the monomer is advantageously polymerizable with the water-swellable polymer particles of the present invention. Suitable $\alpha,\beta$-ethylenically unsaturated monomers include the monomers described above as water-soluble monomers, particularly acrylic acid, methacrylic acid, crotonic acid, and isocrotonic acid, and alkali metal and ammonium salts thereof. Suitable polycarboxylic acids include maleic acid, fumaric acid, and itaconic acid. Suitable acrylamide derivatives include methacrylamide. The preferred monomers include acrylic acid and methacrylic acid, and their respective salt forms, such as alkali metal or ammonium salts.

Should the aqueous solution comprise an $\alpha,\beta$-ethylenically unsaturated monomer, such monomer will preferably be provided in an amount between about 10 weight percent and about 80 weight percents based on the total weight of the aqueous solution. Preferably, the monomer will be provided in an amount between about 10 and about 60 weight percent, based on the total weight of the aqueous solution. Most preferably, the monomer will be provided in an amount between about 15 and about 45 weight percent, based on the total weight of the aqueous solution.

When the aqueous solution comprises an $\alpha,\beta$-ethylenically unsaturated monomer, the aqueous solution is typically prepared by first dispersing the monomer in water. The monomer can be preneutralized and exist as a salt, or as a mixture of the acid and the salt. However, if the monomer is in acidic form, the pH of the solution should then be adjusted to between 4 and 7.

When the aqueous solution comprises an $\alpha,\beta$-ethylenically unsaturated monomer, the amount of such monomer should be selected in concert with the amount of water-swellable particles contained in the second suspension described below. In particular, the amount of $\alpha,\beta$-ethylenically unsaturated monomer provided in the aqueous solution will preferably be such as to provide aggregates containing less than about 33 percent monomer, based on the weight of the aggregates, which translates to a monomer:water-swellable particles ratio in the first and second suspensions of less than about 5:10 or 1:2.

While aggregation of particles may be accomplished by aqueous solutions containing no $\alpha,\beta$-ethylenically unsaturated monomer, the monomer may prove useful in certain applications in which the aggregates will be physically handled. To decrease attrition of the aggregates, the weight ratio of monomer:water-swellable particles will be preferably between about 1:20 and about 1:2. More preferably, the weight ratio of monomer:water-swellable particles will be between about 1:8 and about 1:5.

The particulate suspending aid will preferably comprise an amorphous, highly oil-dispersible, approximately micron and submicron size, substantially water-insoluble particulate material. Typically, the size of the particulate suspending aid ranges from less than one to several microns in diameter. The particulate suspending aid is most preferably hydrophobic silicon dioxide, for example, the particulate material provided by the reaction of silica with polydimethyldichlorosilane. Other useful particulate suspending aids include hydrophobic clays such as the cationic surfactant treated bentonite clays. An example of a hydrophobic clay is sold commercially as Bentone ® 34 by N. L. Industries.

The amount of particulate suspending aid employed influences the the size of the droplets of aqueous solution suspended in the inert hydrophobic liquid, which in turn affects the size of the resultant aggregates or clusters. For example, an aggregate of approximately 1000 microns can be formed when the droplets of the aqueous solution in the first suspension are approximately 50 microns in diameter. To produce preferred droplet sizes, when the aqueous solution contains an $\alpha,\beta$-ethylenically unsaturated monomer, the particulate suspending aid will be generally be provided in an amount between about 0.3 and about 2 weight percent based on the final weight of the composition, more preferably in an amount between about 0.6 and about 1.5 weight percent based on the final weight of the composition. In applications where the aqueous solution does not contain an $\alpha,\beta$-ethylenically unsaturated monomer, the particulate suspending aid will preferably be provided in an amount greater than about 2 weight percent, to prevent excessive agglomeration of the particles.

Optionally, the aqueous solution, regardless of the presence or absence of an $\alpha,\beta$-ethylenically unsaturated monomer, may contain a crosslinking monomer, a chelating agent, and/or one or more initiators.

Suitable crosslinking monomers include organic compounds having two or more ethylenic groups copolymerizable with the water-soluble monomers can be used as the crosslinking monomers. Exemplary crosslinking monomers include diacrylate or dimethacrylate of ethylene glycol, diethylene glycol, triethylene glycol, propylene glycol, 1,4-butane diol, 1,5-pentane diol, 1,6-hexane diol, neopentyl glycol, trimethylol propane and pentaerythritol, triacrylates or trimethacrylates of trimethylol propane and pentaerythritol, tetraacrylates or tetramethacrylates of pentaerythritol, N,N'-methylene-bis-acrylamide, N,N'-methylene-bis-methacrylamide and triallyl isocyanurate, and the like. The preferred crosslinking monomers for the present invention is trimethylolpropanetriacrylate. Typically, the crosslinking monomer is used in amounts ranging from about 0.0001 to 5 parts by weight, based on 100 parts by weight of the $\alpha,\beta$-ethylenically unsaturated monomer used. Preferably, when a crosslinking monomer is employed, it will be provided in an amount less than about 2 weight percent, more preferably in an amount less than about 1 weight percent, based on the weight of the $\alpha,\beta$-ethylenically unsaturated monomer. Crosslinking monomers may be provided in similarly small amounts in an aqueous solution which does not comprise an $\alpha,\beta$-ethylenically unsaturated monomer, without detriment.

As is known in the art, when a metal reactor is employed, a chelating agent is often provided to scavenge free metal ions. One such chelating agent is Versenex TM 80 chelating agent (40 percent aqueous solution of the pentasodium salt of diethylenetriaminepentaacetic acid), available from The Dow Chemical Company.

When the aqueous solution comprises an $\alpha,\beta$-ethylenically unsaturated monomer, it may further comprise one or more initiators. Such initiators should facilitate the polymerization of $\alpha,\beta$-ethylenically unsaturated monomers. Known oxidizing agents/thermal initiators include hydrogen peroxide, potassium persulfate, sodium persulfate, and ammonium persulfate. Other known thermal initiators are the water-soluble azo compounds, such as 2,2'-azobis(2-amidino-propane·HCl). Known reducing agents include sodium erythorbate, ascorbic acid, sodium thiosulfate and sulfur dioxide gas. The total amount of initiators is typically between about 0.01 and about 2 weight percent, based on the weight of the $\alpha,\beta$-ethylenically unsaturated monomer. Should the water swellable particles contain residual initiator, the inclusion of additional initiator into the aqueous solution may be unnecessary. Further, initiators may be provided in similarly small amounts in an aqueous solution which does not comprise an $\alpha,\beta$-ethylenically unsaturated monomer, without detriment.

Optionally, minor amounts of other water-soluble, unsaturated monomers may be present in the aqueous solution such as alkyl esters of the acid monomers. For example, methyl acrylate or methyl methacrylate may be present.

Typically, the first suspension is formed as follows. First, the particulate suspending aid is dispersed in the inert hydrophobic liquid. Second, the aqueous solution is added to the suspending aid/inert hydrophobic liquid dispersion to form a suspension of aqueous solution droplets.

D. The Polymer Particle Suspension (The Second Suspension)

The second suspension comprises a suspension of water-swellable particles in an inert hydrophobic liquid. Suitable inert hydrophobic liquids are set forth above with respect to the first suspension. Typically, the weight ratio of water-swellable particles to inert hydrophobic liquid is not critical. However, for practical purposes, the preferred ratio of water-swellable particles to inert hydrophobic liquid is in the range of about 1:10 to about 2:1.

Figure 9:
Figure 10:
FIG. 10 is a photograph of the clusters of the polymer particles having an unassociated particle size of 50 to 100 mesh (297 to 149 microns).

The size of the aggregates or clusters formed will depend on the size of the polymer particles with which the process begins. The size of the polymer particles with which the process begins further affects the rate at which the resultant clustered composition absorbs fluid. While the inventive process can cluster relatively large particles, see, e.g., FIGS. 9 and 10, preferred particle sizes will permit the achievement of fast fluid absorption rates. Preferably, at least about 70 percent of said particles will be smaller than about 150 microns. More preferably, at least about 50 percent of said particles will be smaller than about 100 microns.

The Process

The inventive process comprises the following steps. First, the first and second suspensions are prepared as set forth above. Second, the first suspension is then slowly added to the second suspension, while the second suspension is agitated and is exposed to polymerization conditions. The polymerization temperature can range from 10° C. to 100 °C., depending upon initiators chosen.

Through the inventive process, the particles are brought together by the aqueous solution. When the aqueous solution contains an α,β-ethylenically unsaturated monomer, it is believed that the monomer polymerizes around the particles. In this manner, the polymerized monomer thus acts as a bonding component for the particles, serving to bond the particles within a cluster either physically or chemically. When the aqueous solution does not contain an α,β-ethylenically unsaturated monomer, it is believed that the aqueous solution swells the particles, rendering them slightly sticky. Such stickiness permits the agglomeration of the particles into clusters. Regardless of whether or not the aqueous solution contains an α,β-ethylenically unsaturated monomer, the particles within each cluster will be retained by a bonding component comprising the residue of the aqueous solution incorporated into the clusters through the inventive process.

The resultant aggregates or clusters can be filtered from the inert hydrophobic liquid, dried in an oven and crushed to a desirable size. A wetting agent can be added after the aggregates have been dried. Such a wetting agent serves to counteract the tendency of the particulate suspending aid to inhibit fluid absorption. Most economically, however, the wetting agent can be added after polymerization, but prior to drying, to allow for a single drying of the polymer.

A wetting agent is defined as an agent which further improves the hydration rate of the polymer and does not reduce the surface tension of a supernatant below 56 dynes/cm (as determined by a standard test method). The "standard test method" is provided by treating dry polymer with 0.4 weight percent of the wetting agent (based on dry weight of polymer); dispersing 1 g of the treated polymer in 150 g of 0.9 percent saline solution; filtering off the supernatant; and determining the surface tension of the supernatant. The surface tension is determined using a duNouy surface tension apparatus.

Ideally, the hydration rate of the polymer is improved without significantly reducing the absorbency properties of the aqueous fluid absorbent material in which the polymer is incorporated. Therefore, suitable wetting agents are non-surfactant or non-detergent type wetting agents such as polyols. Voranol ® 2070 brand wetting agent, available from The Dow Chemical Company, is a preferred example of such a polyol.

Typically, the wetting agent is introduced to the polymer aggregates as an aqueous solution in an amount sufficient to increase the hydration rate of the polymer as compared to a polymer not treated with the wetting agent. Preferably, an amount of from about 0.2 to about 2.0 weight percent of wetting agent based on the weight of polymer will be a sufficient amount. Most preferably, the wetting agent is provided in an amount between about 0.4 and about 0.5 weight percent, based on the weight of clusters.

In the instance when a wetting agent is added prior to drying, and when an α,β-ethylenically unsaturated monomer was used in the first suspension the wetting agent may be provided in an aqueous solution also containing an initiator, such as sodium persulfate. Upon drying, the initiator will react with residual α,β-ethylenically unsaturated monomer, serving to polymerize residual monomer into the polymer network, thus reducing residual monomer levels in the finished product.

In contrast, surface treating the aggregates with an aqueous solution containing the wetting agent after drying entails several energy consuming and time consuming steps. Such a process requires drying off the oil phase and water phase, then spraying the wetting agent solution on the polymer, and finally redrying the polymer.

However, the intermediate drying step can be substantially reduced if, after the polymerization is complete, the water is removed from the suspension, leaving the oil phase remaining with the polymer. A wetting agent in an aqueous solution is then added to the clusters/oil phase. Preferably the solution is added to the polymer aggregates slowly; most preferably the addition occurs over a period of from about 1 to about 30 minutes. The water added through the aqueous solution of the wetting agent can then be vacuum stripped and the oil can be removed by filtration or centrifugation. A final drying yields polymer aggregates having an improved hydration rate over polymer aggregates which have not been treated with the wetting agent.

The absorbent properties of the resultant composition are determined by the following procedures:

1. Hydration rate is tested by evenly spreading 1.0 g of polymer particles over the bottom of a medium sized plastic boat (Fischer catalog 500 ct. #682-160-502). 30 Grams of a 0.9 percent sodium chloride solution is poured over the particles and a timer is simultaneously set. The hydration rate is that time required for complete solution uptake by the polymer.

2. Filtered Free Swell Capacity (FFSC) is determined by allowing 1.0 g of the polymer aggregates or clusters to absorb their limit of 200 g of 0.9 percent sodium chloride solution in 30 minutes, then filtering to separate the hydrated gel polymer from the nonabsorbed salt solution using a Buchner funnel and filter flask evacuated by an aspirator. The excess salt solution which is not absorbed is weighed and subtracted from the original 200 g to yield the filtered free swell capacity value.

3. Water Soluble Polymer Content is determined by extracting 1 g of absorbent polymer for 16 hours with 500 g of 0.9 percent sodium chloride. The swollen polymer is filtered off and the filtrate titrated with hydrochloric acid to determine the level of soluble polymer present.

4. Vortex Rate is determined by weighing 50 grams of a 0.9 percent aqueous sodium chloride solution into a 100 mL beaker. The beaker is placed on a magnetic stirrer such that there is a substantial vortex. To the side of the vortex is added 2 grams of the material to be tested. The time is started when all the material has been added; the time is stopped when the vortex disappears.

Preferably, the aggregates or clusters of the invention will have a vortex rate less than about 30 seconds, more preferably less than about 20 seconds, and most preferably less than about 10 seconds.

EXAMPLES

The following examples illustrate the present invention, without limiting the scope thereof.

Example 1

The first suspension is prepared by suspending the following aqueous solution as droplets in a solution of 100 grams of Isopar ™ M hydrocarbon (deodorized kerosene from Exxon) and 0.25 gram of hydrophobic fumed silica sold as Aerosil ® R-972 from Degussa: 12 grams of acrylic acid, 0.05 gram of trimethylolpropane triacrylate, 0.05 gram of a chelating agent, such as Versenex ™ 80 chelating agent, 15.7 grams of water, 12 grams of a 50 percent solution of sodium hydroxide, and 0.1 gram of t-butyl hydrogen peroxide.

In a one liter reactor, 80 grams of Drytech ® superabsorbent polymer (sodium polyacrylate polymer manufactured by The Dow Chemical Company), having the mixed particle size distribution set forth in Table One, are mixed with 300 grams of Isopar ™ M hydrocarbon.

TABLE ONE

| Mesh | Microns | Percent of Mixture |
| --- | --- | --- |
| <50 | >297 | 7 |
| 50–100 | 149–297 | 20 |
| 100–170 | 88–149 | 20 |
| 170–325 | 44–88 | 28 |
| >325 | <44 | 25 |

The dispersion is suspended using agitation to form a second suspension.

The aggregates or clusters are formed by adding the first suspension to the reactor under constant agitation at 600 rpm, 20° C., and under a flow of sulphur dioxide gas of between 0.1 to 10.0 ppm/min. The clusters are then separated from the hydrocarbon by filtration, treated with an aqueous solution of Voranol ™ 2070 polyol, and then dried in a hot air oven at 100° C. overnight.

The aggregates exhibit a hydration rate of 15 to 20 seconds with no visible gel blocking. A Comparative Example 1 of the Drytech ® (The Dow Chemical Company) non-clustered superabsorbent polymer, having the same mixed particle size distribution, exhibit a hydration rate of greater than 10 minutes with visible gel blocking.

The composition of this example of the invention exhibits a FFSC of 26 g/g, a water soluble polymer content of 7 percent, and a vortex rate of about 11 seconds.

Examples 2–5

Polymer particles having a particle sizes smaller than 325 mesh (44 microns) in the case of Example 2, between 170 and 325 mesh (44 to 88 microns) in the case of Example 3, between 100 and 170 mesh (88 to 149 microns) in the case of Example 4, and between 50 and 100 mesh (149–297 microns) in the case of Example 5, are associated similarly by the method used to produce the clusters of Example 1. In the case of the composition of Example 2, the hydration rate, FFSC, water soluble levels, and vortex rate of the clusters, are evaluated in a similar manner to those clusters of Example 1. The hydration rate for the clusters of Example 2 is 2 to 5 seconds with no visible gel blocking, the FFSC is 28, the water-solubles level is 7, and the vortex rate is 4 seconds. Comparative Example 2, which consists of samples of the unassociated polymer particles of Example 2 having a particle size smaller than 325 mesh (44 microns), is evaluated in a similar manner to those of the Comparative Example 1. The samples of Comparative Example 2 exhibit gel blocking, rendering the hydration rate and vortex rate extremely long.

Example 2 and Comparative Example 2 illustrate that for particles of smaller than 325 mesh (44 microns), the clusters of the invention exhibit a hydration rate of between 2 and 5 seconds whereas the unassociated particles of that same mesh size undesirably gel block.

The following Table Two sets forth the size distribution of the particles from which the clustered compositions of Examples 1–5 are formed, and the associated vortex rates of such compositions.

TABLE TWO

| Example | Particle size (mesh) | Particle size (microns) | Vortex Rate (seconds) |
| --- | --- | --- | --- |
| 1 | mixed (per Table One) | mixed (per Table One) | 11 |
| 2 | >325 | <44 | 4 |
| 3 | 170–325 | 44–88 | 9 |
| 4 | 100–170 | 88–149 | 30 |
| 5 | 50–100 | 149–297 | 62 |

Example 6

Polymer particles having a mixed particle size are clustered similarly to those polymers in Example 1. However, the clusters are prepared with a first suspension which does not contain an α,β-ethylenically unsaturated monomer, and in which the amount of hydrophobic fumed silica used in the process is increased to one gram. Thirty grams of the clusters are then treated with a wetting agent by adding 5 grams of 0.4 percent Voranol ® 2070 polyol in water solution. The clusters are then dried in an oven.

The FFSC of the Voranol ® 2070 polyol treated clusters is 33 g/g, the water-solubles level is 11 percent and the hydration rate is 20 seconds with no visible gel blocking. Example 6 illustrates that although the hydration rate of the clusters is quicker when a monomer solution is used in the process to prepare the clusters as is shown in Example 1, the clusters of Example 3 exhibit a fast hydration rate without gel blocking even though a monomer such as acrylic acid was not used in the first suspension.

Example 7

The first suspension is prepared by suspending the following aqueous solution as droplets in a solution of 25 pounds of Isopar ™ M hydrocarbon and 140 grams of hydrophobic fumed silica sold as Aerosil ® R-974 by Degussa: 3405 grams of acrylic acid, 14 grams of trimethylolpropane triacrylate, 14 grams of a chelating agent, such as Versenex ™ 80 chelating agent, 4313 grams of water, 3405 grams of a 50 percent solution of sodium hydroxide, and 14 grams of t-butyl hydrogen peroxide.

In a 50-gallon reactor, Drytech ® superabsorbent polymer, available from The Dow Chemical Company, having been sized and/or screened to form 50 pounds of water-swellable particles having a particle size smaller than 80 mesh (177 microns), is mixed with 160 pounds of Isopar ™ M hydrocarbon to form a second suspension.

The clusters are formed by adding the first suspension to the reactor under constant agitation at 20° C. Polymerization occurs for about an hour. After the polymerization is complete, the reactor is vacuum stripped to 90° C., and is then cooled to 70° C. A solution of 20 grams of persulfate, 140 grams of Voranol ® 2070 polyol and 4400 grams of water is then added to the clusters at 70° C. over 90 minutes. The clusters are then vacuum stripped and separated from the inert hydrophobic liquid by filtration. The clusters are then dried overnight in a hot air oven at 100° C.

The resultant aggregates exhibit a hydration rate of 10 seconds and a water solubles level of 7 percent.

What is claimed is:

1. A process for preparing water-swellable polymer clusters for absorbing aqueous fluids, comprising:
   (a) dispersing an aqueous solution comprising an $\alpha,\beta$-ethylenically unsaturated monomer and an amorphous oil dispersible substantially water-insoluble particulate suspending aid in an inert hydrophobic liquid to form a first suspension;
   (b) dispersing water-swellable polymer particles in an inert hydrophobic liquid to form a second suspension; and
   (c) slowly adding said first suspension, to said second suspension, while said second suspension is agitated and is exposed to polymerization conditions, such that said particles are bonded to each other, whereby discrete clusters of said water-swellable particles are formed, said particles being associated to each other in a random packing configuration, said particles being spatially distributed to allow aqueous absorption by said particles without gel blocking of said aqueous fluids at the surfaces of said clusters.

2. The process of claim 1, wherein the $\alpha,\beta$-ethylenically unsaturated monomer is acrylic acid, methacrylic acid, crotonic acid, isocrotonic acid, or a salt thereof.

3. The process of claim 1, wherein said aqueous solution additionally comprises a crosslinking monomer of diacrylate or dimethacrylate of ethylene glycol, diethylene glycol, triethylene glycol, propylene glycol, 1,4-butane diol, 1,5-pentane diol, 1,6-hexane diol, neopentyl glycol, trimethylol propane or pentaerythritol, triacrylates or trimethacrylates of trimethylol propane or pentaerythritol, tetracrylates or tetramethacrylates of pentaerythritol, N,N'-methylene-bis-acrylamide, N,N'-methylene-bis-methacrylamide or triallyl isocyanurate.

4. The process of claim 1, wherein said inert hydrophobic liquid is perchloroethylene, methylene chloride, liquid aromatic or aliphatic hydrocarbons of 4 to 15 carbons per molecule or mixtures thereof.

5. The process of claim 1, wherein said particulate suspending aid is hydrophobic silicon dioxide.

6. The process of claim 1, wherein said $\alpha,\beta$-ethylenically unsaturated monomer is present in an amount of about 15 to about 45 weight percent based on total weight of the aqueous solution.

7. The process of claim 1, comprising the additional steps of (d) drying the clusters, (e) adding a wetting agent to the clusters, and (f) crushing the clusters.

* * * * *